US 6,571,620 B2

(12) United States Patent
Moisio

(10) Patent No.: US 6,571,620 B2
(45) Date of Patent: Jun. 3, 2003

(54) METHOD AND ARRANGEMENT FOR KEEPING MEASURING DEVICE CLEAN

(75) Inventor: Hannu Moisio, Kangasala (FI)

(73) Assignee: Metso Automation Oy, Helsinki (FI)

( * ) Notice: Subject to any disclaimer, the term of this patent is extended or adjusted under 35 U.S.C. 154(b) by 0 days.

(21) Appl. No.: 10/115,544

(22) Filed: Apr. 3, 2002

(65) Prior Publication Data
US 2002/0144546 A1 Oct. 10, 2002

(30) Foreign Application Priority Data
Apr. 9, 2001 (FI) .............................. 20010734

(51) Int. Cl.[7] .............................. G01N 23/16; B05C 5/02
(52) U.S. Cl. ...................................................... 73/159
(58) Field of Search ............................................ 73/159

(56) References Cited

U.S. PATENT DOCUMENTS

| 3,662,174 A | * | 5/1972 | McMullen et al. ...... 250/358.1 |
| 4,194,840 A | * | 3/1980 | Lucas et al. ................ 250/216 |
| 4,266,142 A | | 5/1981 | Crawford ............... 250/559.01 |
| 4,602,160 A | * | 7/1986 | Mactaggart .............. 250/341.5 |
| 4,966,788 A | * | 10/1990 | Pell ............................ 427/210 |
| 5,049,216 A | * | 9/1991 | Shead et al. ................ 156/208 |
| 5,233,195 A | * | 8/1993 | Hellstrom et al. ........ 250/360.1 |
| 5,421,529 A | | 6/1995 | Hans .......................... 242/470 |
| 5,479,720 A | | 1/1996 | Hellstrom et al. ....... 33/501.02 |
| 5,563,737 A | | 10/1996 | Kamrat ...................... 359/509 |
| 5,669,158 A | * | 9/1997 | Murray et al. ................ 34/393 |
| 5,879,626 A | | 3/1999 | Watterson et al. ............ 422/62 |
| 6,038,836 A | * | 3/2000 | Focke et al. ................ 250/200 |

FOREIGN PATENT DOCUMENTS

| DE | 199 18 011 | 10/2000 | ............. B08B/3/02 |
| EP | 0 383 486 | 8/1990 | ............. D21F/1/32 |
| EP | 0 816 077 | 1/1998 | ............ B41F/35/00 |
| EP | 0 974 828 | 1/2000 | .......... G01N/21/15 |
| FR | 2 604 199 | 3/1988 | ............. D21F/1/32 |

OTHER PUBLICATIONS

Copy of Finnish Office Action for Appl. No. 20010734 dated Feb. 11, 2002.
Copy of European Search Report for Appl. No. EP 01007833 completed Jun. 10, 2002.

* cited by examiner

Primary Examiner—Helen Kwok
Assistant Examiner—David Rogers
(74) Attorney, Agent, or Firm—Alston & Bird LLP

(57) ABSTRACT

A method and an arrangement for keeping a measuring device clean, the measuring device being arranged to measure at least one property of a moving web and comprising at least one measuring head with at least one measuring element that is cleaned with cleaning agent during measurement.

25 Claims, 2 Drawing Sheets

METHOD AND ARRANGEMENT FOR KEEPING MEASURING DEVICE CLEAN

BACKGROUND OF THE INVENTION

1) Field of the Invention

The invention relates to a method of keeping a measuring device clean, the measuring device being arranged to measure at least one property of a moving web and comprising at least one measuring head with at least one measuring element.

The invention further relates to an arrangement for keeping a measuring device clean, the measuring device being arrangeable to measure at least one property of a moving web and comprising at least one measuring head with at least one measuring element.

2) Description of Related Art

In papermaking, characteristics of paper quality, such as thickness, are measured while a paper web to be manufactured is moving in a paper machine. Characteristics of paper quality are typically measured by means of traversing measuring devices, wherein measuring sensors are arranged in measuring carriages that traverse the paper web in the transverse direction thereof over the entire web width. However, measuring devices can also be stationary, in which case they constantly measure the same point in the transverse direction of the paper web.

Dirt and dust build up as the paper web is formed and dried, and when the web moves at a high speed in the machine, dirt and dust are spread around the paper machine. This dirt and dust sticks onto measuring elements or measuring windows of the measuring device, which causes distortions in the measurement result. Furthermore, in the case of high-speed paper machines and thin paper grades the dirt increases the number of holes the measuring device produces in the web. The problem of dirt has been further aggravated by the increased use of recycled pulp.

Cleanliness of measuring devices is very important in order to obtain an accurate measurement result. For example, the thickness of paper produced by a machine for producing newsprint is typically about 70 $\mu$m, and the external accuracy of measurement to be achieved varies between 0.3 and 1 $\mu$m. Dust and dirt gathering on the surface of a measuring element or a measuring window thus hinder the operation of a thickness gauge, in particular. Dirt also causes deviations in the measurement accuracy of profile, since even during one cycle of measurement which covers one back-and-forth movement over the paper web and which can last, for example, one minute, the thickness of the layer of dust and dirt gathering on the surface of the measuring element or window can change, at worst, dozens of micrometers.

The effect of dirt and dust on the measurement result has been compensated by standardizing the measuring devices at regular intervals. However, in view of an accurate measurement result this method is highly unreliable since new dirt accumulates and old dirt is removed continuously, and the amount of dirt can thus vary a great deal between rounds of standardization. The standardization trend exhibits great changes, yet there may have been even greater variations between instants of standardization than what the trend shows, such variations resulting from temporary accumulation of dirt.

Traversing measuring devices are currently cleaned during the standardization of the measuring device, i.e. when the measuring carriage and the devices therein are removed from the area of measurement outside the edge of the paper web. The measuring device in question and any other measuring devices in the same carriage are out of operation and no measurement results are thus obtained during cleaning. The measuring carriage is moved outside the web at desired intervals, typically for example once an hour, which is rather seldom regarding the accuracy of the measurement result. The measuring elements or windows can be cleaned for example manually by wiping them with a cleaning cloth or by blowing pressurized air onto the surface of the measuring element or window. Manual cleaning is laborious and requires service personnel. On the other hand, blowing pressurized air is not sufficient to remove accumulated dirt that is stuck onto the surface of the measuring element or window, such as a paper coating agent or resin provided in recycled pulp. The prior art also teaches blowing of pressurized air to keep a measuring window of a measuring device clean during measurement. An example of such an arrangement is disclosed in EP 0,974,828.

BRIEF SUMMARY OF THE INVENTION

An objective of the present invention is to provide a new type of method and arrangement for keeping a measuring device clean.

The method according to the invention is characterized by cleaning the measuring element with cleaning agent during measurement.

The arrangement according to the invention is characterized in that the arrangement comprises means for feeding cleaning agent to clean the measuring element during measurement.

According to the basic idea of the invention, a measuring device arranged to measure at least one property of a moving web and comprising at least one measuring head with at least one measuring element, is kept clean by feeding cleaning agent to clean the surface of the measuring element during measurement. According to a preferred embodiment of the invention, the measuring element is kept clean by feeding cleaning agent to the surface of the measuring element or the moving web and by bringing the web and the measuring element into contact with each other, so that the moving web wipes the surface of the measuring element with the cleaning agent. According to another preferred embodiment of the invention, the measuring element is arranged to move up and down in the elevation of the measuring head, and the surface of the measuring element is brought into contact with the moving web by lifting or lowering the measuring element. According to a third preferred embodiment of the invention, the measuring element is fixed to the measuring head and the moving web is in continuous contact with the surface of the measuring element. According to a fourth preferred embodiment of the invention, cleaning agent is supplied to the surface of the moving web or the measuring element in the form of sprays with freely adjustable duration and interval. According to a fifth preferred embodiment of the invention, cleaning agent is continuously supplied to the surface of the moving web or the measuring element. According to a sixth preferred embodiment of the invention, cleaning agent is continuously supplied to the surface of the measuring element in order to prevent dust from sticking to the surface.

An advantage of the invention is that the cleaning of the measuring element and thus the measuring head does not require the measuring device to be moved outside the web, but the device can be cleaned and/or kept clean during the use thereof in measuring web properties. Therefore the measurement does not have to be interrupted, and high accuracy of measurement can be maintained even in dirty conditions. The use of the cleaning agent helps remove even persistent dirt from the measuring element, thus reducing the number of holes and other defects caused in the web by the measuring element. Depending on the speed at which the measuring element becomes soiled and on the conditions of use, cleaning agent can be fed either continuously or in the form of sprays with freely adjustable duration and intervals. The amount of cleaning agent needed to keep the measuring element clean is so small that it has no substantial effect on the web properties.

The arrangement according to the invention can be used similarly in connection with board manufacture, and in this specification the term 'paper' also refers to board and pulp.

BRIEF DESCRIPTION OF THE SEVERAL VIEWS OF THE DRAWINGS

The invention will be described in more detail in the accompanying drawings, in which.

DETAILED DESCRIPTION OF THE INVENTION

Figure 1:
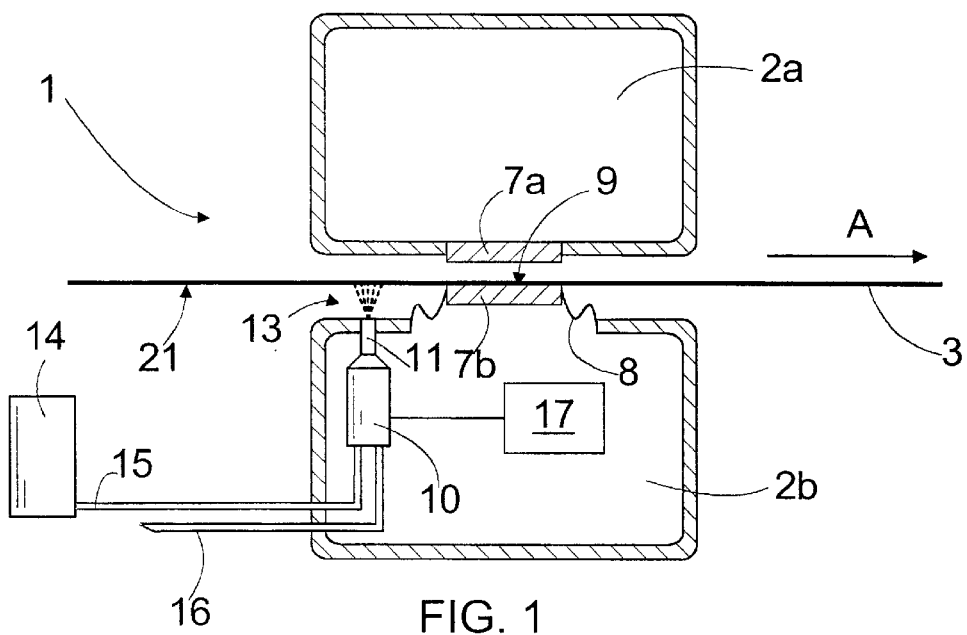
FIG. 1 shows schematically an arrangement according to the invention for keeping a measuring device clean, viewed in partial cross-section from the side of the measuring device.
Figure 5:
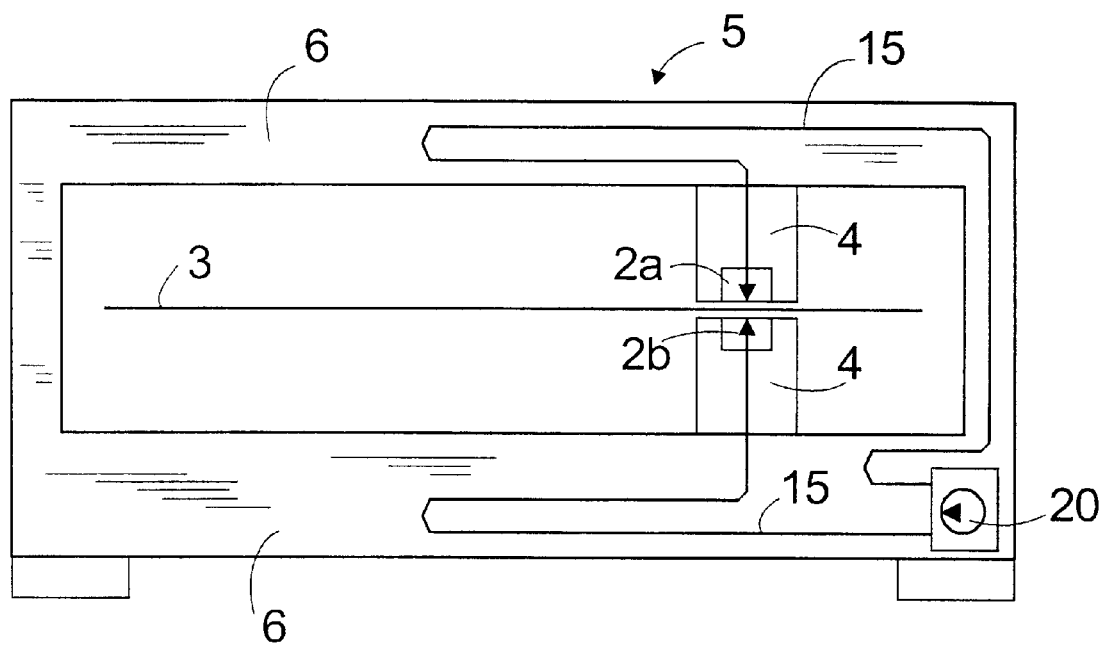
FIG. 5 is a schematic front view of a measuring frame in a paper machine.

FIG. 1 is a schematic side view, in partial cross-section, of an arrangement for keeping a measuring element of a measuring device clean, the device measuring at least one property of a moving web. The measuring device 1 shown in FIG. 1 is arranged to measure the thickness of a paper web 3 as the web moves in the direction of arrow A, i.e. in the machine direction. For the sake of clarity, the paper web 3 is shown in FIG. 1 in a substantially thicker form than it really has compared to the structure of the measuring device 1. The measuring device 1 comprises a first measuring head 2a and a second measuring head 2b, between which the paper web 3 is moving. As shown schematically in FIG. 5, the measuring heads 2a, 2b are provided in measuring carriages 4 that are arranged to reciprocate substantially continuously along beams 6 of a measuring frame 5 transversely to the machine direction of the paper machine along the entire width of the paper web 3. The measuring heads 2a, 2b can also be fixed either to the beams 6 or to some other suitable structure in the paper machine, so that they measure only one point of the paper web 3 in the lateral direction thereof. The first measuring head 2a is provided with a first measuring element 7a, and the second measuring head 2b is provided with a second measuring element 7b. The first measuring element 7a can be for example a coil, and the second measuring element 7b can be a button formed of a suitable material, such as a sapphire-coated metal plate, so that the distance between the measuring elements 7a and 7b can be determined in a manner known per se. The first measuring element 7a is fixed to the first measuring head 2a. The second measuring element 7b in turn is connected to the second measuring head 2b via a flexible membrane 8. The flexible membrane 8 enables the second measuring element 7b to move towards or away from the first measuring element 7a for example as the thickness of the paper web 3 varies. FIG. 1 shows the measuring element 7b in a situation where the upper surface 9 of the element 7b touches the lower surface 21 of the paper web 3. However, the measuring element 7b is not necessarily in continuous contact with the paper web 3. Different measuring elements or sensors and their use to measure thickness or some other property of the paper web 3 are known per se to those skilled in the art, wherefore they will not be discussed in greater detail herein. Moreover, the term 'measuring element' also includes a measuring window of an optical or a radiometric measuring device, for instance. In addition to the second measuring element 7b, the first measuring element 7a can be connected movably via a flexible membrane to the first measuring head 2a.

Figure 2:
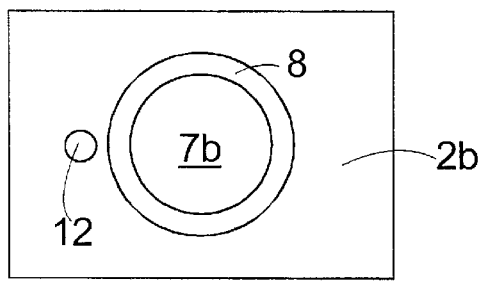
FIG. 2 shows schematically the arrangement according to FIG. 1, viewed from above a second measuring head of the measuring device.

In the arrangement of FIG. 1, which is shown schematically in FIG. 2 viewed from above the second measuring head 2b, the measuring head 2b is provided with a pump 10 for removing dust, dirt and other impurities gathering to the upper surface 9 of the measuring element 7b, the pump operating as a feeding unit for feeding cleaning agent to clean the measuring element 7b. The pump 10, which can be for example an injection pump, is arranged in the measuring head 2b right before the measuring element 7b in the direction of travel of the paper web 3. The measuring head 2b is provided with an opening 12, via which a spray of cleaning agent 13 supplied from a nozzle 11 of the pump 10 is able to flow outside the measuring head 2b and further to the lower surface 21 of the paper web 3. After the measuring element 7b has been lifted into the position shown in FIG. 1, where the measuring element 7b touches the lower surface 21 of the paper web 3, the paper web 3 moves forward and simultaneously wipes the upper surface 9 of the measuring element 7b clean by means of the cleaning agent contained on the lower surface 21 of the web. The dust and dirt gathering in the measuring element 7a can also be removed by means of the cleaning agent according to the invention by providing the measuring head 2a with similar means for supplying cleaning agent as shown in FIGS. 1 and 2. The paper web 3 can thus be made to move either near the measuring element 7a or to be in contact with the element continuously or intermittently. The measuring element 7a can also be connected to the measuring head 2a via a flexible membrane.

The cleaning agent is stored in a cleaning agent tank 14, from which it is supplied via a transfer conduit 15 to the pump 10. The transfer conduit 15 can be for example a regular hose, which has very high bending and chemical resistance. The cleaning agent tank 14 can be arranged e.g. in the measuring carriage 4 or in the measuring frame 5. Pressurized air is also supplied to the pump 10 via a pressure air conduit 16 in order to split the cleaning agent in the spray of cleaning agent 13 into sufficiently small droplets. The pressure air conduit 16 can be for example a flexible hose. If pressurized air or purge air is supplied to the measuring carriage 4 for some other reason than for splitting the cleaning agent into droplets, these sources of pressurized air and purge air can also be used to reduce the agent into droplets. In such a case, for example when an existing measuring carriage is provided with means for feeding cleaning agent, the equipment does not require a new pressure air conduit. The operation of the pump 10 is preferably controlled by a control unit 17 based on semiconductor technology and comprising as adjustable variables the duration and interval of the sprays of cleaning agent 13. If the amount of dirt and dust gathering for example during one minute is 20 μm, and the desired measurement accuracy allows a dirt layer of at most 1 micrometer at the surface of the measuring element, the interval between the sprays of cleaning agent 13 could be set in this case to three seconds, for example. The duration and flow volume rate of the spray of cleaning agent 13 are determined so that the amount of the agent to be sprayed does not affect the properties of the paper web 3. In this case the duration of the spray of cleaning agent 13 could be for example 0.1 s, and the amount of the agent to be sprayed could be e.g. 33 ml per hour. Cleaning agent can also be sprayed continuously, which means that the spray 13 is continuous.

The nozzle 11 of the pump 10 can be implemented in several manners. The nozzle 11 is preferably knife-like. A knife-like nozzle produces a spray of cleaning agent 13, which is very narrow in the direction of travel of the paper web 3 denoted by arrow A, but wide in the transverse direction of the web 3. If the area to be cleaned is very wide in the lateral direction of the paper web 3, two or more pumps 10 and openings 12 can be provided in parallel in the measuring head 2b, so that a very wide spray of cleaning agent can be supplied to the lower surface 21 of the paper web 3. Furthermore, one pump 10 can be used to supply cleaning agent via several nozzles 11 and openings 12. According to one implementation of the nozzle 11, when the measuring element 7b does not touch the paper web 3, the spray of cleaning agent 13 is supplied directly to the upper surface 9 of the measuring element 7b so as to prevent dust and dirt from sticking thereto. If desired, the dry paper web 3 can be brought into contact with the measuring element 7b, whereafter the paper web 3 wipes away the cleaning agent together with the dirt and dust from the upper surface 9 of the measuring element 7b.

An advantage of the invention is that the measuring element and thus the measuring head can be cleaned or kept clean while the measuring device keeps measuring properties of a moving web without interruptions. Consequently, high accuracy of measurement can be maintained continuously even in dirty conditions of use. By means of cleaning agent even persistent dirt can be easily wiped off the measuring element, which reduces the number of holes or other defects caused by the measuring element in the web.

Figure 3:
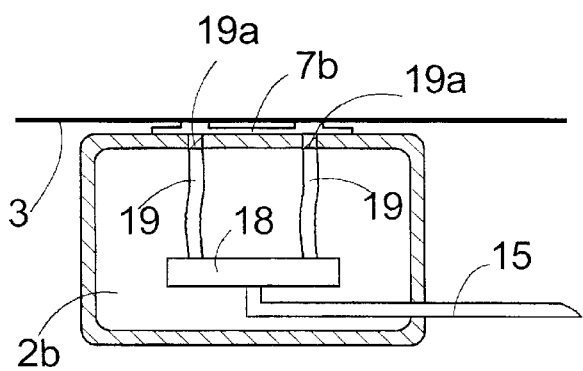
FIG. 3 shows schematically another arrangement according to the invention, viewed in partial cross-section from the front of the measuring head of the measuring device.
Figure 4:
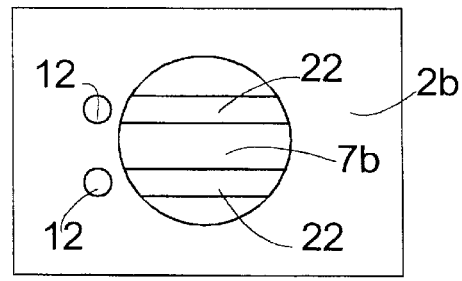
FIG. 4 shows schematically the arrangement according to FIG. 3, viewed from above the measuring head.

FIG. 3 shows schematically another arrangement for cleaning the measuring element 7b, viewed in partial cross-section from the front of the measuring head 2b. FIG. 4 shows schematically a top view of the measuring head 2b according to FIG. 3. In the arrangement shown in FIGS. 3 and 4, the measuring element 7b is fixed to the measuring head 2b, and the paper web 3 is in continuous contact with the measuring element 7b. The measuring element 7b comprises two contact surfaces 22, which protrude from the rest of the structure of the element. The measuring head 2b is provided with two openings 12 at the contact surfaces 22 right before the measuring element 7b with respect to the direction of travel of the web, and cleaning agent can be supplied to the paper web 3 via the openings. The measuring head 2b comprises a bypass manifold 18 used as a feeding unit. A feed hose 19 is provided from the bypass manifold 18 to each opening 12. The cleaning agent is transferred from the cleaning agent tank 14 via the transfer conduit 15 to the bypass manifold 18, which distributes the agent into feed nozzles 19a. In the case of the thickness gauge disclosed in this example, the material of the feed nozzles 19a is selected such that the nozzles do not affect the measurement result. The cleaning agent tank 14 can be located for example at the end of the beam 6, as shown schematically in FIG. 5, and the cleaning agent is thus transferred to the bypass manifold 18 at the measuring head 2b by means of a pump 20 provided in the cleaning agent tank 14. The pump 20 can also be located in the transfer conduit 15. Cleaning agent can be administered continuously, i.e. a continuous flow of cleaning agent is supplied to the paper web 3, or cleaning agent can be fed at predetermined intervals. Thus, the pump 20 can be of either feeding or continuous type, and the output of the pump can be adjusted. Depending on the consumption of cleaning agent, a small cleaning agent tank 14 and a pump 20 optionally provided therein can also be arranged in the measuring carriage 4. The pump 20 can be any one of a number of pump alternatives. The pump 20 can be for example a peristaltic pump, a piston pump or a gear pump. Furthermore, the transfer of cleaning agent does not necessarily require a pump, but a pressurized water network, such as a cooling water conduit, is also suitable for the purpose. In such a case the nozzle 11 can be designed to feed cleaning agent, or the nozzle 11 can provide a continuous spray of cleaning agent. A feed nozzle 11 is controlled by the aforementioned control unit 17.

The cleaning agent is non-toxic and odorless, it provides good wetting, and it also has low surface tension. The agent is also volatile, wherefore it does not remain in the paper. A particularly suitable cleaning agent is water, since the agent can thus be obtained from the cooling water conduit of the measuring device 1 and no separate cleaning agent tank is needed. The cleaning agent can also be a solvent fulfilling the aforementioned requirements, or a mixture of a solvent and water. In such a case the solvent requires a separate tank or a feeding device. The only essential requirement for the composition of the cleaning agent is that the agent should not interfere with the operation of the measuring device, i.e. in the case of the thickness gauge set forth in the examples, the cleaning agent must have such magnetic properties that it does not affect the measurement result. The cleaning agent can also prevent accumulation of dirt, which means that cleaning agent is supplied to the surface of the measuring element 7b to prevent dirt and dust from sticking thereto. Therefore the arrangement according to the invention can be applied in optical measuring devices where the measuring element, or the measuring window thereof, does not touch the surface of the moving web. In such a case the measuring element is cleaned by spraying cleaning agent to the surface of the measuring element or between the web and the element to prevent dirt from sticking to the surface of the element. The cleaning agent to be sprayed can naturally also remove dirt from the surface of the measuring element.

The drawings and the related description are only intended to illustrate the inventive idea. The details of the invention can vary within the scope of the claims. Thus, instead of a paper web 3, the moving web to be measured can be a kind of plastic membrane or some other plastic-based web. However, the moving web is preferably a paper, board or pulp web. It is also evident that the arrangement shown in FIGS. 1 and 2 can be used in connection with a stationary measuring element, and the arrangement shown in FIGS. 3 and 4 can be used in connection with a moving measuring element. Furthermore, depending on the property of the moving web to be monitored and the measurement method of the measuring elements required to monitor the property, the measuring device can comprise only one measuring head instead of two, and the measuring element can be arranged either immovably or movably in the measuring head. Instead of the measuring head, the unit for feeding cleaning agent can be placed in the measuring carriage, such that the feeding unit feeds cleaning agent to the web before the web moves between the measuring heads. The measuring element can also be provided with small channels, through which the cleaning agent can be conducted to the surface of paper as the measuring element touches the paper web.

That which is claimed:

1. An apparatus adapted to measure a property of a moving web, said apparatus comprising:
    a liquid cleaning agent;
    a measuring element disposed adjacent to the web and configured to be capable of at least momentarily contacting the web;
    a nozzle disposed adjacent to the measuring element and upstream thereof with respect to the moving web, the nozzle being configured to direct the liquid cleaning agent onto at least one of the measuring element and the web such that the liquid cleaning agent and the at least momentary contact between the measuring element and the web cooperate to clean the measuring element.

2. An apparatus according to claim 1 wherein the liquid cleaning agent comprises water.

3. An apparatus according to claim 1 wherein the measuring element is configured to be movable toward and away from the web.

4. An apparatus according to claim 1 wherein the measuring element configured so as to be in substantially continuous contact with the web.

5. An apparatus according to claim 1 further comprising a measuring head configured to house the measuring element.

6. An apparatus according to claim 5 wherein the measuring head is further configured to house the nozzle.

7. An apparatus according to claim 5 wherein the measuring head is stationary and the measuring element is configured to be movable with respect to the measuring head.

8. An apparatus according to claim 1 further comprising a cleaning unit in communication with the nozzle, the cleaning unit being configured to store the liquid cleaning agent and being capable of providing the liquid cleaning agent to the nozzle.

9. An apparatus according to claim 8 further comprising a measuring head configured to house the nozzle and the cleaning unit.

10. An apparatus according to claim 8 further comprising a control unit in communication with the cleaning unit, the cleaning unit being responsive to the control unit so as to selectively provide the liquid cleaning agent to the nozzle for a selected duration.

11. An apparatus according to claim 8 wherein the cleaning unit is configured to substantially continuously provide the liquid cleaning agent to the nozzle.

12. An apparatus according to claim 1 further comprising a measuring carriage having the measuring element and the nozzle operably engaged therewith, the measuring carriage being configured to be transversely movable with respect to the moving web.

13. An apparatus according to claim 1 wherein the nozzle is configured as a bypass manifold having a plurality of nozzle openings for directing the liquid cleaning agent onto at least one of the measuring head and the web.

14. An apparatus according to claim 1 wherein the measuring element is configured to measure the thickness of the web.

15. A method of cleaning an apparatus adapted to measure a property of a moving web, the apparatus including at least one measuring element disposed adjacent to the web, said method comprising:
    directing a liquid cleaning agent through a nozzle onto at least one of the measuring element and the web, the nozzle being disposed adjacent to the measuring element and upstream thereof with respect to the moving web; and
    at least momentarily contacting the measuring element with the web such that the liquid cleaning agent and the at least momentary contact between the measuring element and the web cooperate to clean the measuring element.

16. A method according to claim 15 wherein directing a liquid cleaning agent through a nozzle further comprises directing water through a nozzle.

17. A method according to claim 15 wherein at least momentarily contacting the measuring element with the web further comprises moving the measuring element toward and away from the web.

18. A method according to claim 15 wherein at least momentarily contacting the measuring element with the web further comprises maintaining the measuring element in substantially continuous contact with the web.

19. A method according to claim 15 wherein the measuring element is housed in a stationary measuring head, and wherein at least momentarily contacting the measuring element with the web further comprises moving the measuring element with respect to the measuring head toward and away from the web.

20. A method according to claim 15 wherein the measuring element and a cleaning unit are housed in a measuring head and the cleaning unit is configured to store the liquid cleaning agent, and wherein directing a liquid cleaning agent through a nozzle further comprises providing the liquid cleaning agent to the nozzle with the cleaning unit.

21. A method according to claim 20 wherein directing a liquid cleaning agent through a nozzle further comprises selectively providing the liquid cleaning agent to the nozzle, and for a selected duration, with the cleaning unit in response to a control unit in communication with the cleaning unit.

22. A method according to claim 20 wherein directing a liquid cleaning agent through a nozzle further comprises substantially continuously providing the liquid cleaning agent to the nozzle with the cleaning unit.

23. A method according to claim 15 wherein the measuring element and the nozzle are operably engaged with a measuring carriage, and wherein directing a liquid cleaning agent through a nozzle further comprises providing the liquid cleaning agent to the nozzle while the nozzle and measuring element are moved transversely with respect to the moving web by the measuring carriage.

24. A method according to claim 15 wherein directing a liquid cleaning agent through a nozzle further comprises directing a liquid cleaning agent through a nozzle configured as a bypass manifold having a plurality of nozzle openings.

25. A method according to claim 15 further comprising measuring the thickness of the web with the measuring element.

* * * * *

UNITED STATES PATENT AND TRADEMARK OFFICE
CERTIFICATE OF CORRECTION

PATENT NO.      : 6,571,620 B2                                        Page 1 of 1
DATED           : June 3, 2003
INVENTOR(S)     : Moisio It is certified that error appears in the above-identified patent and that said Letters Patent is hereby corrected as shown below:

<u>Column 7,</u>
Line 30, after "element" insert -- is --.

Signed and Sealed this

Seventh Day of October, 2003

JAMES E. ROGAN
*Director of the United States Patent and Trademark Office*